United States Patent [19]

Li et al.

[11] Patent Number: 5,047,337

[45] Date of Patent: Sep. 10, 1991

[54] CERAMIDE-GLYCANASE

[76] Inventors: Su-Chen Li; Yu-Teh Li, both of Tulane University Medical Center 1430 Tulane Ave., New Orleans, La. 70112

[21] Appl. No.: 113,024

[22] Filed: Oct. 23, 1987

[51] Int. Cl.$^5$ .................. C12P 19/04; C12P 7/64; C12P 13/02; C12N 9/24

[52] U.S. Cl. .................. 435/101; 435/200; 435/129; 435/134

[58] Field of Search .................. 435/200, 201, 74, 84, 435/100, 101, 129, 134

[56] References Cited

U.S. PATENT DOCUMENTS 4,390,630 6/1983 Sawyer et al. .................. 435/226
4,588,576 5/1986 Gasic .................. 424/95

FOREIGN PATENT DOCUMENTS 62-122587 3/1987 Japan.

OTHER PUBLICATIONS

Li, S-C, et al., (1986) Biochem. Biophys. Res. Comm. 141, 346-352.
Ito, M., et al., (1986) J. Biol. Chem. 261(30), 14278-14282.
Li, Y-T, et al., (1987) Biochem. Biophys. Res. Comm. 149, 167-172.
Roscoe O. Brady, Andrew E. Gal, Julian N. Kanfer and Roy M. Bradley, "The Journal of Biological Chemistry", 240:3766-3770, (1965).
Yu-Teh Li and Shu-Chen Li, "Advances in Carbohydrate Chemistry and Biochemistry", 40:235-285, (1982).
Shu-Chen Li, "Methods in Enzymology", 28:702-713, (1982).
Li, "Comparative Biochemistry and Physiology", 14:275-279, (1965).
Momcilo Miljkovic and Cara-Lynne Schengrund, "Carbohydrate Research", 155:175-181, (1986).
Sulitzeanu, "Advances in Carbohydrate Research", 44:1-42, (1985).

*Primary Examiner*—Jacqueline Stone
*Assistant Examiner*—Charles L. Patterson
*Attorney, Agent, or Firm*—Pravel, Gambrell, Hewitt, Kimball & Krieger

[57] ABSTRACT

Ceramide-glycanase which cleaves the entire oligosaccharides intact from glycosphingolipids and alkylglycolipids. The enzyme does not hydrolyze monosaccharides from these glycoconjugates. The enzyme is obtained from the muscle tissue of annelids such as earthworms and leeches by homogenization in water, ammonium sulfate fractionation, gel permeation chromatography, and hydrophobic interaction chromatography, and is essentially free from exo-glycosidase activity. Also disclosed is a method for obtaining oligosaccharides by hydrolysis of glycolipids, alkylglycolipids, and glycosphingolipids by the ceramide-glycanase.

38 Claims, 3 Drawing Sheets

E  Lc Gb3Gb4Gb5 S1  Lc Gb3 Gb4 Gb5 S2
              +   +   +   +
              E   E   E   E

E  Lc Gb3Gb4Gb5 S1  Lc Gb3Gb4Gb5 S2
              +   +   +   +
              E   E   E   E

E  M3 M2 M1 D1a S1  M3 M2 M1 D1a S2
              +   +   +   +
              E   E   E   E

E  M3 M2 M1 D1a S1  M3 M2 M1 D1a S2
              +   +   +   +
              E   E   E   E

CERAMIDE-GLYCANASE

This invention was made with Government support under grants and/or contracts awarded by the National Science Foundation and the National Institutes of Health, and the Government has certain rights in this invention.

FIELD OF THE INVENTION

This invention relates to glycosidases, and particularly to annelid ceramide-glycanases which yield intact oligosaccharides and ceramides from glycosphingolipids.

BACKGROUND OF THE INVENTION

Many glycosidases are known. These glycosidases include both exo- and endo-glycosidases which are generally highly specific for particular glycosides. In addition, such glycosidases generally produce monosaccharides or degraded oligosaccharides from the glycoside substrate. Thus, in the typical analytical method or catabolism of glycosphingolipids, a series of exo-glycosidases are involved which sequentially hydrolyze the nonreducing end of the saccharide chain. For example, exo-glycosidases obtained from earthworms, such as $\beta$-galactodisase, $\alpha$-galactosidase, $\alpha$- N-acetylgalactosaminidase and $\beta$-hexosaminidase, were reported in Li et al, Comp. Biochem. Physiol., vol. 14, pp. 275-279 (1965). Heretofore, there has been no enzyme known which will hydrolyze the glycosidic bond of glycolipids between an oligosaccharide and a lipid.

SUMMARY OF THE INVENTION

It has now been discovered that there is an enzyme occurring, for example, in annelids which is capable of cleaving glycosphingolipids to yield essentially intact oligosaccharide and ceramide. This enzyme can be separated from the exo-glycosidases occurring in annelids by protein fractionation and chromatography, and is referred to herein as ceramide-glycanase.

Accordingly, the invention provides ceramide-glycanase, preferably substantially pure, and particularly essentially free of exo-glycosidase. The ceramide-glycanase is preferably characterized in that it hydrolyzes glycosphingolipid at the glycosidic linkage between the ceramide and glycan thereof when the glycan comprises at least two glycosidically linked saccharides. The preferred ceramide-glycanase may be further characterized in that it yields essentially intact oligosaccharide and ceramide from such glycosphingolipids. The preferred ceramide-glycanase may be still further characterized in that it is soluble in 0.1 M acetate buffered to pH 6.0; has an optimum enzymatic pH between about 4.5 and about 6.5; and an isoelectric point at about pH 5.

In another aspect, the invention provides a ceramide-glycanase essentially free of exo-glycosidases, prepared by a method including preparing aqueous extract from annelid tissue, precipitating protein from said extract, and substantially removing exo-glycosidases from the protein precipitate by molecular sieve chromatography. Suitable annelids include, for example, earthworms, leeches and nereis.

In a further aspect, the invention provides a method for preparing ceramide-glycanase essentially free of exo-glycosidase. The method includes the steps of extracting annelid tissue with water, fractionating protein from the aqueous extract, and substantially removing exo-glycosidases from the fractionated protein by molecular sieve chromatography.

In a still further aspect, the invention provides a method for hydrolyzing a glycolipid. The method includes the steps of contacting the glycolipid with an effective amount of ceramide-glycanase to produce an essentially intact oligosaccharide. Suitable glycolipid substrates in this method have an oligosaccharide glycosidically bonded to a hydrophobic aglycon and include, for example, glycosphingolipids and alkyl-glycolipids.

DESCRIPTION OF THE INVENTION

Briefly, the ceramide-glycanase of the present invention releases the entire oligosacharide intact from glycosphingolipid, together with ceramide. This is in sharp contrast to the heretofore known exo- and endo-glycosidases which are highly specific for glycosides and produce either monosaccharides or partially degraded oligosaccharides. The ceramide-glycanase also has hydrolytic activity against other glycoconjugates in which the aglycon is hydrophobic and similarly yields intact oligosaccharide therefrom.

The ceramide-glycanase of the present invention may be obtained from at least two different sources. One contemplated source of ceramide-glycanase is bacterial cultivation in the presence of glycosphingolipids such as gangliosides, e.g., bovine brain acetone powder or bovine brain gangliosides, as an inducer for the expression of the ceramide-glycanase by the bacteria. However, this source is not preferred because of the necessity of inducing expression of ceramide-glycanase and the difficulties associated with such fermentation of the bacteria and recovery of the enzyme therefrom.

A preferred source for ceramide glycanase is annelids, particularly annelid muscle tissue. Annelids such as species of leeches (e.g. Hirudinea and Macrobdella) and earthworms (e.g. Lumbricidae) have been found to be relatively high in ceramide-glycanase, and although muscle of such annelids also typically contains exo-glycosidases, the annelid ceramide-glycanase can be readily separated from the exo-glycosidases by purification. Other annelids contemplated as suitable sources for ceramide-glycanase in addition to leeches and earthworms include species of Nereis. As used herein, the term "annelid ceramide-glycanase" includes enzymatically active analogues, homologues, isomers, mutants and fragments of ceramide-glycanases which occur naturally in annelids, whether obtained from annelids, from a natural source other than annelids or from a synthetic source. Annelid ceramide-glycanase obtained from annelids such as leeches an earthworms is readily distinguished from that obtained from the ganglioside-induced actinomycetes reported in Ito et al, The Journal of Biological Chemistry, vol. 261, pp. 14278-14282 (Oct. 25, 1986), for example, by solubility in 0.1M sodium acetate buffer at pH 6.0 and broad optimum enzymatic activity at a pH of about 4.5-6.5 as opposed to about 6.0 for the bacterial enzyme.

Annelid ceramide-glycanase obtained from leeches and earthworms hydrolyzes neutral glycosphingolipids such as lactosyl-ceramide, globotriaosyl-ceramide, globotetraosyl-ceramide, globopentaoyl-ceramicde, lacto-N-neotetraoyl-ceramide and the like, to liberate intact the respective oligosaccharides lactose, globotriaose, globotetraose, globopentaose and lacto-N-neotetraose. This annelid ceramide-glycanase also hydrolyzes acidic glycosphingolipids such as the gangliosides GM3, GM2, GM1, GD1a, GT1, and sulfated glycolipids such as 3-sulfo-lactosyl ceramide, and the like, to liberate intact the respective sialo-oligosaccharides and sulfo-oligosaccharides. In the nomenclature of gangliosides, the letter G (GD1a) refers to ganglioside, the second letter (CD1a) indicates the number of sialic acid (NeuAc) groups (M=monosialo, D=disialo, and T=arisialo). The numeral following the letters (GD1a) is 5-n, where n is the number of neutral sugar residues. The final letter following the numeral GD1a) indicates the position of the sialic acids on the ganglioside. For Example, GD1a contains two sialic acids. One of them links to the internal galactose and the other to the terminal galactose. GD1b is an isomer of GD1a which also contains two sialic acids. However, they are linked to each other and the resulting two sialic acid chain is in turn linked to the internal galactose. On the other hand, the ceramide-glycanase will not generally hydrolyze monohexosylceramides such as galactosylceramide and glucosylceramide.

The ceramide-glycanase preferably has one or more of the following properties: an isoelectric point at about pH 5.0; an optimum pH between about 4.5 and about 6.5 for hydrolysis of glycosphingolipids and is solubilized in 0.1M sodium actate buffer at pH 6.0 in the absence of detergents such as octyl glucoside.

The ceramide-glycanase is also preferably substantially pure, i.e., it should have a specific activity of at least about 1 unit per mg of protein, more preferably at least about 50 units per mg, and especially 2000–4000 units per mg. Ultimately, the enzyme may have an activity as high as 6,000 units/mg or more. As used herein one unit of ceramide-glycanase activity is the amount of enzyme that hydrolyzes 1 nmol of GM1 or GM2 in one hour in a standard assay containing 30 nmol of radioactive-labelled substrate and 200 mg sodium taurodeoxycholate in 200 $\mu$l total volume of assay solution buffered at the optimum pH over the range of 4.5–6.5 at 37° C. In an especially preferred embodiment, the ceramide-glycanase is essentially free of exo-glycosidases, particularly $\alpha$-N-acetylgalactosaminidase, $\beta$-galactosidase and $\beta$-hexosaminidase. As used herein, the ceramide-glycanase is essentially free of exo-glycosidase when the amount of monosaccharide released from a glycosphingolipid such as GM1 treated with the ceramide-glycanase is relatively minor compared to the amount of oligosaccharide released therefrom. Preferably, the molar fraction of monosaccharide released is less than 1 percent of the total saccharide released, and especially less than 0.1 percent.

In another preferred embodiment, the ceramide-glycanase is prepared from annelids by a method which includes preparing an extract from annelid tissue, fractionating protein from the extract containing ceramide-glycanase activity, purifying the frationated protein by molecular sieve chromatography, and recovering a purified protein having ceramide-glycanase activity of at least 1 unit per mg. This method is described in more detail hereinbelow.

In the method of the invention for preparing ceramide glycanase, the initial step is the preparation of an extract from a suitable source. Suitable sources include annelids such as, for example, earthworms, leeches, nereis, and the like, and especially the muscle tissue thereof. Although the digestive and other organs may contain some ceramide-glycanase, the enzyme is more abundant in the muscle tissue. The muscle tissue may be separated from the other organs in most annelids by conventional dissection techniques. If desired, for example when the organism cannot be easily dissected, the whole organism may be used.

An extract is prepared from the annelid by conventional techniques. Typically, the annelid or muscle tissue thereof is homogenized with a protein solvent, preferably water. When an aqueous extract is prepared, distilled water is desirably used as the solvent, although other aqueous solvents such as saline, with or without pH buffer, may also be employed. The amount of solvent employed is not particularly critical and about 5 ml of solvent per gram of homogenized tissue has been found to be suitable for this purpose. The extract is obtained from the insoluble homogenized annelid tissue by centrifugation, filtration or the like, as is conventional in the art.

The protein contained in the extract may then be fractionated therefrom by conventional techniques, such as, for example, fractionation or precipitation with ammonium sulfate or its equivalent. Typically, the extract is treated with sufficient ammonium sulfate to initiate protein precipitation therefrom up to an amount sufficient to saturate or nearly saturate the extract solution, e.g., 30–80 percent saturation with ammonium sulfate. This mixture is then allowed to stand for a period of time, typically overnight, to complete the protein precipitation. Other solutes in the extract such as lower molecular weight peptides and amino acids, oligosaccharides, monosaccharides, and the like, do not generally precipitate from the extract under these conditions. The precipitated protein is conveniently recovered from the solvent by centrifugation, although if desired, other conventional techniques such as filtration could be employed as an alternative.

The protein precipitate is then purified by chromatography. Column materials contemplated as suitable include conventional permeation gels, ion exchange resins, hydrophobic interaction gels, and the like. Of these, gel permeation chromatography is preferred. An especially preferred chromatographic purification includes the use of two columns, the first having a permeation gel packing and the second having a hydrophobic interaction packing. For example, using Sepharose 6B as the first column yields an eluate fraction containing a relatively greater ceramide-glycanase activity per unit weight of protein in the fraction than other eluate fractions. Preferably, this fraction contains at least 1 unit of ceramide-glycanase per mg of protein, and especially at least 4 units/mg when the annelid is earthworm or Hirudinae sp., and at least 50 units/mg when the annelid is Macrobdella sp. The ceramide-glycanase in this fraction may be concentrated by conventional ultrafiltration. Alternatively, the enzyme activity can be concentrated by ammonium sulfate precipitation. Ammonium sulfate may conveniently be removed from the precipitate by dissolving in a minimal amount of solvent, for example, 50 mM sodium phosphate buffer, pH 6.0, and dialyzing against the same solvent.

However, the protein recovered from the gel permeation chromatography may also contain significant quantities of exo-glycosidases such as $\alpha$-N-acetylgalactosaminidase, $\beta$-galactosidase, $\beta$-hexosaminidase, and the like. These exo-glycosidases may be removed by hydrophobic interaction chromotography on a high affinity column, such as a hydrophobic column, for example, octyl-sepharose, phenyl-sepharose and the like. A technique found to be suitable includes passing the fraction from the gel permeation chromatography, containing both ceramide-glycanase and exo-glycosidase, through an octyl-sepharose column equilibrated with 50 mM sodium phosphate buffer, pH 6.0, and washing the column with additional buffer. The exo-glycosidases are not generally bound to the column and are substantially removed by the washing, whereas a major portion of the ceramide-glycanase may be eluted and recovered by subsequently washing the column with a suitable solvent, such as, for example, buffer containing 40% ethylene glycol and detergents such as 0.1% Triton X-100 and 1% octyl glucoside. If desired, the ceramide-glycanase so recovered may be concentrated by ultrafiltration and purified by dialysis to remove ethylene glycol and detergents.

The ceramide-glycanase recovered in this manner may be further purified if desired. However, for most purposes the ceramide-glycanase obtained by the foregoing method is sufficiently pure since it contains relatively little exo-glycosidase so that hydrolysis of a suitable substrate therewith will not result in the formation of significant quantities of monosaccharides. The earthworm ceramide-glycanase obtained in this manner may have a specific activity of 50 units per mg of protein or more, while that from leeches such as *Macrobdella decora* may be as high was 2,000–4,000 units/mg.

In the melhod of the invention for hydrolyzing glycolipid and obtaining oligosaccharides, a substrate is contacted with ceramide-glycanase. Suitable substrates contemplated generally include oligosaccharides glycosidically bonded to a hydrophobic moiety, such as, for example, a hydrocarbyl radical having at least about 8 carbon atoms. The hydrocarbyl radical may be substituted or unsubstituted, and exemplary radicals include $C_8$–$C_{26}$ alkyls and alkenyls such as octyl, decyl, dodecyl, stearyl, oleyl, behenyl, palmityl, vaccenyl, linoleyl, arachidyl, cerotyl, lignoceryl, myristyl, palmitoleyl, $\alpha$-linolenyl, arachidonyl, sphingosyl, and $\alpha$-hydroxy substitued derivatives thereof, and the like; ceramides such as N-palmitoyl-1-sphingosyl, N-stearoyl-1-sphingosyl, N-behenoyl-1-sphingosyl, N-lignoceroyl-1-sphingosyl, N-palmitoyl-1-sphingosyl, N-oleoyl-1-sphingosyl, N-vaccenoyl-1-sphingosyl, and the like. As exemplary substrates there may be mentioned sphingolipids such as lactosylceramide, globotriaosylceramide, globotetraosylceramide, globopentaosylceramide, GT, GM3, GM2, GM1, GD3, GD2, GD1a, GD1b, $IV^3$-$\alpha$-N-glycolylneuraminosyl-neolactotetraglycosylceramide, $VI^3$-$\alpha$-N-acetylneuraminosyl-neolactohexaglycosylceramide, polyglycosylceramide, and the like; and alkylglycolipids such as octyl lactoside, oleyl lactoside, stearyl lactoside, myristyl lactoside, and the like.

The ceramide-glycanase may be either from ganglioside-induced bacteria or annelids, but annelid ceramide-glycanase is preferred because of its ready solubility in buffer solution and ease of preparation. The enzyme does not need to be highly purified, but preferably has a specific ceramide-glycanase activity of at least 1, more preferably at least 50, and especially at least 2000, units per mg of protein. In most instances, the ceramide-glycanase is preferably essentially free of exo-glycosidases to the extent that no significant amounts of monosaccharides are produced from the substrate.

To effect the enzymatic hydrolysis of the substrate, the ceramide-glycanase is placed in contact with the substrate, typically in a liquid medium in which both the enzyme and the substrate are soluble or well-dispersed. The hydrolysis medium may be, for example, buffered saline, preferably at or near the optimum pH for the particular enzyme. Generally, an aqueous medium will need to contain a detergent or surfactant such as a bile salt, for example, sodium taurodeoxycholate, sodium taurocholate, crude bile salts, or the like. The use of such detergents for enzymic hydrolysis of glycosphingolipids in aqueous systems is conventional in the art because glycolipids generally aggregate to form micelles. It has been found suitable in most instances to use about 1 mg/ml of sodium taurodeoxycholate. However, a detergent may not be necessary in nonaqueous media, or when the aglycon of the substrate is not highly hydrophobic, e.g. alkylglycolipids having about 8–12 carbon atoms in the aglycon, such as octyl lactoside.

The amount of ceramide-glycanase required depends primarily on the amount of substrate and the time in which it is desired to complete the hydrolysis, although the hydrolysis rate can be affected by conditions in the hydrolysis medium such as pH, temperature and the presence or absence of activators and/or inhibitors of the enzyme. For example, in one hour 10 units of ceramide-glycanase will hydrolyze one-third of 30 nmoles of GM2 in 0.2 ml total volume of 50 mM sodium actate buffer at pH 4.5 containing 200 mg sodium taurodeoxycholate.

If desired, the oligosaccharide and/or the aglycon of the glycoconjugate substrate can be recovered by any conventional techniques for recovering such products well known in the art, such as, for example, solvent extraction, normal and reverse phase chromatography, thin layer chromatography, and the ike. In analytical applications, for example, the hydrolysis products of glycosphingolipids can be separated by solvent extraction with 5 volumes chloroform:methanol (2:1), evaporation to dryness, and observation by conventional thin-layer chromatography employing various visualizing stains such as resorcinol for sialic acid-containing oligosaccharides and glycoconjugates, found in the aqueous phase, diphenylamine for neutral oligosaccharides and glycoconjugates found in the aqueous phase, and Coomassie brilliant blue for the hydrophobic aglycons such as ceramide generally found in the organic phase, while the enzyme is typically insoluble in such solvent extraction medium and remains at the interface.

It is also contemplated that therapeutically useful oligosaccharides can be recovered from the hydrolysis of gangliosides which have been used in treatment of peripheral neuropathies, such as the drug available under the designation CRONAXIAL from Fidia. Such oligosaccharides may be more therapeutically effective than the corresponding gangliosides since the oligosaccharide would be more readily soluble in body fluids and it is likely that the ceramide is not necessary for therapeutic activity. Similarly, such oligosaccharides may also enchance the properties of skin creams and other cosmetics in which glycosphingolipids have been used. It is also well known that many tumor specific antigens are expressed through the oligosaccharide moieties of glycosphingolipids Sulitzeanu, Dov, *Human Cancer-Associated Antigens: Present Status and Implications for Immunodiagnosis*, Advances in Cancer Research Vol. 44, pp. 1–42 (1985). It is also contemplated that ceramide-glycanase may be useful to release oligosaccharides from the lipid extract of tumor tissues. The analysis of the released water soluble oligosaccharides can facilitate the identification of tumor specific glycosphingolipids and also the diagnosis of different tumors. Alternatively ceramide-glycanase can be used to release the oligosaccharides from the purified tumor specific glycosphingolipids. The oligosaccharides can be subsequently linked to a biopolymer, such as polylysine or albumin, to enhance its antigenicity for the production of antibodies which, in turn, can be used to facilitate the identification of tumor specific glycosphingolipids.

BRIEF DESCRIPTION OF THE DRAWINGS

FIG. 6 is photographs of thin-layer chromatograms showing the ceramides (A) and the oligosaccharides (B) from various gangliosides in which the incubation conditions are identica to those described for FIG. 5, and in which in chromatogram A, lane E is enzyme; lane S1 is standard ceramide containing nonhydroxy fatty acids; lane S2 is standard ceramide containing β-hydroxy fatty acids; lane M3 is GM3; lane M2 is GM2; lane M1 is GM1; lane D1a is GD1a; and in chromatogram B the lanes are identical to those in chromatogram A except that lane S-1 is standard containing sialyllactose (top) and oligosaccharides from GM2; and lane S-2 is oligosaccharides from GM1 (top) and GD1a.

EXAMPLE 1

Isolation of Ceramide-Glycanase from Leech, *Hirudo medicinalis*

Figure 1:
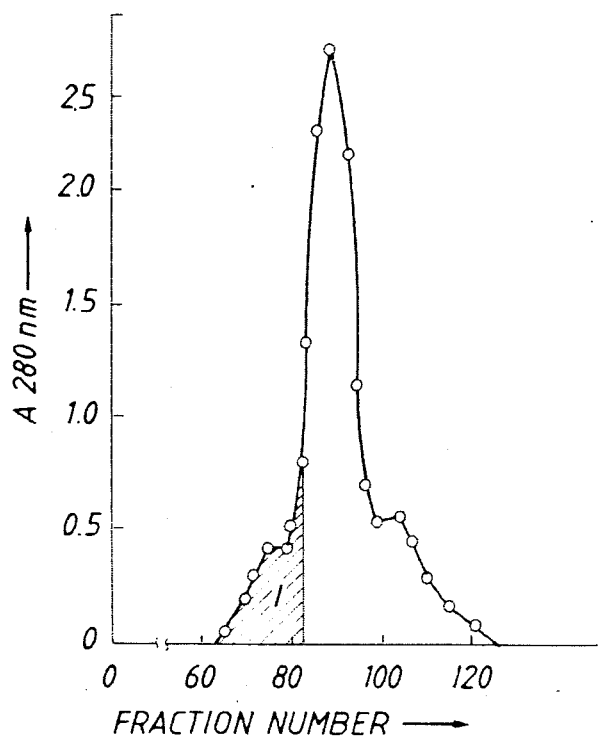
FIG. 1 is a chromatogram of the Sepharose-6B filtration of the crude enzyme precipitated between 30% and 80% $(NH_4)_2SO_4$ saturation in Example 1 in which the shaded area indicates eluate fractions containing ceramide-glycanase and exo-glycosidases.

Unless otherwise indicated, the isolation of the enzyme was carried out at a temperature between 0 and 5° C. Centrifugation was routinely carried out at 13,000× g for 20 minutes using a Sorvall RC5C refrigerated centrifuge. Seven leeches (*Hirudo medicinalis*) weighing 23 g were rinsed with distilled water, minced and homogenized with 5 volumes of 50 mM sodium phosphate buffer, pH 7.0, with a Polytron homogenizer and centrifuged to obtain 120 ml of clear extract. The extract was brought to 30% saturation with solid $(NH_4)_2SO_4$. After standing for two hours, the mixture was centrifuged to remove the precipitated protein. The supernatant was brought to 80% saturation with solid $(NH_4)_2SO_4$. The precipitated protein from this fraction was collected the next day by centrifugation, and dissolved in 30 ml of 50 mM sodium acetate buffer, pH 4.5, to obtain a crude enzyme preparation which contained 588 mg protein. The crude enzyme preparation was divided into 5-ml portions and applied to a Sepharose-6B column (2.5×90 cm; Pharmacia) previously equilibrated with 50 mM sodium acetate buffer, pH 4.5. The column was eluted with the same buffer at 25 ml per hour and 5-ml fractions were collected. The elution profile is shown in FIG. 1. The ceramide-glycanase activity together with various exo-glycosidase activities were eluted in the first protein peak (peak 1). Peak I was concentrated to a volume of 4 ml which contained 20.3 mg protein, using an Amicon ultrafiltration unit with a PM-10 membrane. This fraction was subsequently applied to an Octyl-Sepharose column (1×5 cm; Sigma); which had been equilibrated with 50 mM sodium acetate, pH 4.5. The column was washed with the same buffer to remove the unadsorbed protein. Under this condition, most exo-glycosidases were not retained by the column. The ceramide-glycanase retained by the column was eluted with 15 ml 1% octyl-β-glucoside dissolved in the same buffer, concentrated by ultrafiltration using an Amicon PM-10 membrane and dialyzed exhaustively against the same buffer to yield 2 ml of a solution which contained 5.6 mg purified ceramide-glycanase.

EXAMPLE 2

Isolation of Ceramide-Glycanase from Leech, *Macrobdella decora*

*Hirudo medicinalis* leech is a European leech. It has been found that ceramide-glycanase can also be isolated from the North American leech, *Macrobdella decora* according to the procedure similar to that described in Example 1.

*Macrobdella decora* leeches weighing 452 g were homogenized with 2.26 l of distilled water in a Waring blender and centrifuged to obtain 2.46 l clear extract.

The extract was brought to 80% saturation with solid $(NH_4)_2SO_4$. The precipitated protein was collected the next day by centrifugation and dissolved in 258 ml of sodium phosphate buffer, pH 6.0, to obtain a crude enzyme preparation which contained 9.4 g protein. The crude enzyme preparation was divided into 32 ml portions and applied to a Sepharose-6B column (5.0×90 cm; Pharamacia) equilibrated with 50 mM sodium phosphate buffer, pH 6.0. The column was eluted with the same buffer at 60 ml per hour and 18 ml fractions were collected. The elution profile is similar to that shown in FIG. 1. The ceramide-glycanase activity together with various exo-glycosidase activities were eluted in the first protein peak (peak I). The ceramide-glycanase in peak I was precipitated by adding $(NH_4)_2SO_4$ to 80% saturation. The precipitated fractions of peak I from nine separate sepharose-6B columns as described above were combined and dissolved in 50 mM sodium phosphate buffer, pH 6.0 to obtain 100 ml protein solution which contained 95,760 units of ceramide-glycanase and 1.68 g of protein. This solution was applied to an octylsepharose column (2.5×10 cm; Sigma), which had been equilibrated with 50 mM sodium phosphate buffer, pH 6.0. The column was washed with the same buffer to remove the unadsorbed proteins. The column was subsequently washed with 200 ml volumes of 50% ethylene glycol followed by two liters of water. All exo-glycosidases were completely washed off from the column under this condition. Ceramide-glycanase retained by the column was then eluted with 300 ml of 1% octyl-glucoside dissolved in 50 mM sodium phosphate, pH 6.0. The eluate which contained ceramide-glycanase was concentrated by ultrafiltration and then dialyzed against 50 mM sodium phosphate buffer, pH 6.0 to obtain 9 ml of solution which contained 85,950 units of ceramide-glycanase and 31 mg of protein. The ceramide-glycanase isolated by this procedure was found to have no exo-glycosidase activity. The substrate specificities of *Macrobdella decora* leech cermaide-glycanase were found to be similar to that isolated from *Hirudo medicinalis* leech in Example 1.

EXAMPLE 3

Hydrolysis of Glycolipids with Leech Enzyme

Assays were performed in 10×75 mm glass tubes. The incubation mixture contained the following components in 0.2ml: glycolipid substrate, 30 nmol; sodium acetate buffer (50 mM), pH 4.5; sodium taurodeoxycholate, 200 µg; and 20 µl of the enzyme solution of Example 1 or 2. Glycolipid substrates included LacCer, GbOse3Cer, GbOse4Cer, GbOse5Cer, nLcOse4Cer, $GM_3$, $GM_2$, $GM_1$, $GD1a$ and $GT1$. After the mixture was incubated at 37° C. for a preset time, the reaction was terminated by adding 5 volumes of chloroform:methanol (2:1). The mixture was vortexed and briefly centrifuged to separate the organic phase (lower) from the aqueous phase (upper). Under this condition the enzyme protein became insoluble and stayed at the interface. The organic and the aqueous phases were separately withdrawn from the tube and evaporated to dryness. For detection of the released oligosaccharide, the aqueous phase was analyzed by thin-layer chromatography using n-butanol:acetic acid:$H_2O$ (2:1:1) as the developing solvent. Sialic acid-containing glycoconjugates were revealed by resorcinol spray, while glycoconjugates which contained neutral sugars were visualized by diphenylamine spray. For the detection of the ceramides released by the enzyme, the organic phase was analyzed by thin-layer chromatography using chloroform:methanol (9:1) as the developing solvent. The ceramides were revealed by staining the plate with Coomassie brilliant blue. The chromatograms are seen in FIGS. 2 and 3.

For quantitative analysis of the oligosaccharide released, the assay was performed in a 1.5 ml polypropylene tube; the reaction mixture was similar to that described above except 30 nmol of [$^3$H]-labeled $GM_1$ ($1.5 \times 10^4$ cpm) was used. After incubation, the reaction was terminated by heating the tube in a bath of boiling water for three minutes, followed by the addition of 20 µl of 1 M KCl and 200 µl of a slurry of Nucleosil C18 to adsorb the unreacted $GM_1$ and ceramide. The mixture was vortexed, allowed to stand for 15 minutes at room temperature, and then centrifuged in a microcentrifuge at 12,000 r.p.m. An aliquot of the supernatant containing the liberated radioactive oligosaccharide was mixed with scintillation fluid, and the radioactivity was measured by liquid scintillation counting. Exo-glycosidases were assayed by using p-nitrophenyl-glycosides as substrates. Protein was determined by the method of Lowry et al, *J. Biol. Chem*, 193: 265-274 (1951), using bovine serum albumin as standard.

The pH optimum was determined to be between pH 4 and 5 for the Example 1 enzyme, and between 4.5 and 6.5 for the Example 2 enzyme, for the release of tritiated oligosaccharide from the labeled $GM_1$. The hydrophobic nature of the enzyme is indicated by its adsorption on octyl-sepharose. The enzyme was found to require the presence of sodium taurodeoxycholate to carry out the cleavage of the linkage between the ceramide and the sugar chain in the glycosphingolipids used in this example.

Figure 2A:
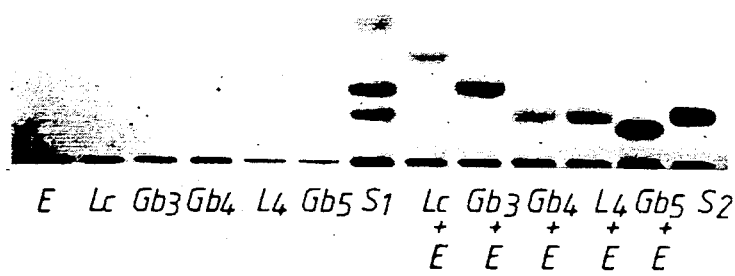
FIG. 2 is photographs of thin-layer chromatograms showing the oligosaccharides (A) and the ceramides (B) released by ceramide-glycanase from various neutral glycosphingolipids for 6 h at 37° C. as described in Example 3, in which in chromatogram A, lane E is enzyme; lane Lc is LacCer; lane $Gb_3$ is $GbOse_3Cer$; lane $Gb_4$ is $BgOse_4Cer$; lane $L_4$ is $nLcOse_4Cer$; lane $Gb_5$ is $GbOse_5Cer$; lane S1 is standard containing GalNAc, lactose, trisaccharide from $GbOse_3Cer$, and tetrasaccharide from $GbOse_4Cer$ (top to bottom); lane S2 is lacto-N-neotetraose; and in chromatogram B the lanes are identical to those in chromatogram A except that lane S1 is standard containing ceramides with nonhydroxy faty acids (top band) and α-hydroxy fatty acids (bottom band); and lane S2 is standard ceramide containing α-hydroxy fatty acids.
Figure 2B:
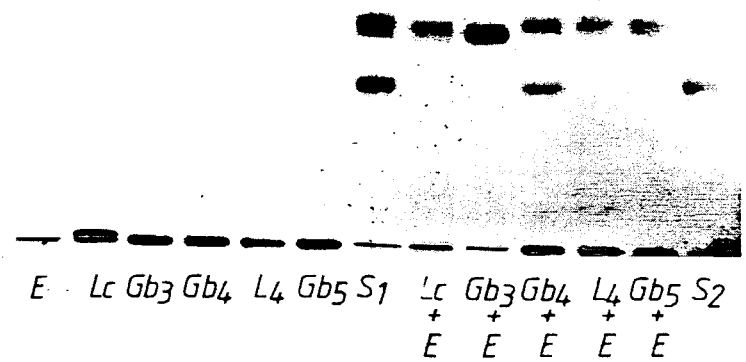

As shown in FIG. 2A, leech ceramide-glycanase was able to liberate the intact oligosaccharide from LacCer, GbOse3Cer, GbOse4Cer, GbOse5Cer, and nLcOse4Cer. The disaccharide released from LacCer by the enzyme showed TLC mobility identical to that of lactose and it was converted to Gal and Glc by jack bean β-galactosidase. The enzyme released an oligosaccharide from nLcOse4Cer with TLC mobility identical to that of lacto-N-neotetraose. The trisaccharide and tetrasaccharide released from GbOse3Cer and GbOse4Cer, respectively, showed TLC mobilities identical to the globotriaose and globotetraose prepared from these two glycosphingolipids by ozonolysis. The oligosaccharide released from GbOse5Cer moved slower on TLC than that from GbOse4Cer. These oligosaccharides released by the enzyme were subsequently characterized by sequential enzymatic hydrolysis using fig α-galactosidase, limpet α-N-acetylgalactosaminidase and the β-galactosidase and β-hexosaminidase both from jack bean. Their structures were found to be consistent with that found in the parent glycosphingolipids. The corresponding ceramides liberated from these glycosphingolipids are shown in FIG. 2B. In the case of GbOse4Cer, which contained both types of fatty acids, the enzyme iberated ceramides both with and without α-hydroxy fatty acids. From the other glycosphingolipids only ceramides without α-hydroxy fatty acids were detected.

Figure 3A:
FIG. 3 is photographs of thin-layer chromatograms showing the oligosaccharides (A) and the cermides (B) released by ceramide-glycanase from various gangliosides as described in Example 3, in which chromatograms A, lane E is enzyme; lane M3 is GM3; M2 is GM2; lane M1 is GM1 ; lane D1a is GD1a; lane T is GT1; lane S1 is standard containing sialic acid, sialyllactose and the oligosaccharide from GM2 (top to bottom); lane S2 is standard containing oligosaccharides from GM1 (top band) and from GD1a (bottom band); and in chromatogram B the lane indications used are identical to those in chromatogram A except lane S1 is standard ceramide containing non-hydroxy fatty acids; and lane S2 is standard ceramide containing α-hydroxy fatty acids.
Figure 3B:

FIG. 3A shows the hydrolysis of gangliosides by leech ceramide-glycanase. The enzyme liberated an intact sialic acid containing oligosaccharide from $GM_3$, $GM_2$, $GM_1$, $GD1a$ and $GT1$. From $GM_3$, the enzyme released an oligosaccharide with thin-layer chromatography mobility identical to that of sialyllactose. Clostridial neuraminidase converted this sialo-oligosaccharide to a disaccharide which was subsequently hydrolyzed by jack bean β-galactosidase to produce Gal and Glc. From each of the gangliosides, GM2, GM1, and GD1a, the enzyme released an intact sialic acid containing oligosaccharide with thin-layer chromatography mobility identical to the oligosaccharide obtained by ozonolysis from the respective ganglioside. The oligosaccharide released from GT1 was slower in thin-layer chromatography mobility than that from GD1a. The corresponding liberation of the ceramides from these gangliosides is shown in FIG. 3B. The ceramides released from these gangliosides had thin-layer chromatography mobilities corresponding to the standard ceramide with nonhydroxy fatty acids.

EXAMPLE 4

Isolation of Ceramide-Glycanase from Earthworms

Figure 4:
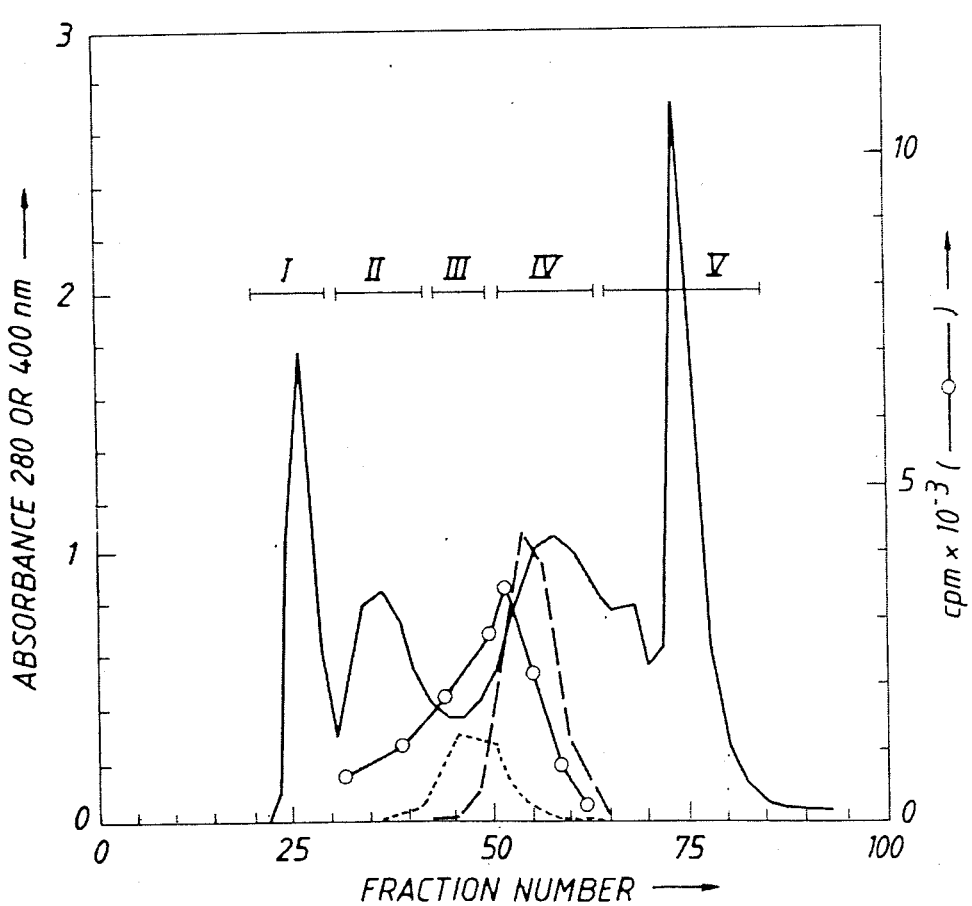
FIG. 4 is a chromatogram of the Sepharose-6B filtration of the earthworm crude enzyme preparation of Example 4 (solid line) and illustrates β-galactosidase activity (dashed line), β-hexosamindase activity (long-dashed line), and ceramide-glycanase activity (circles).

Earthworms were dissected by making a longitudinal dorsal incision, separating the muscle tissue to reveal the intact digestive tract. The digestive tract and other organs were carefully removed from the muscle. The muscle was rinsed with distilled water to wash off the digestive fluid. Unless otherwise indicated, the preparation of the enzyme was carried out at a temperature between 0° and 5° C. Centrifugation was routinely carried out at 13,000× g for 20 minutes using a Sorvall RC5C refrigerated centrifuge. The muscle from six earthworms (14 g) was homogenized with 5 volumes of distilled water with a Polytron homogenizer to obtain 70 ml of clear extract. The extract was brought to 80% saturation with solid ammonium sulfate. The precipitated protein was collected the next day by centrifugation, dissolved in 12 ml of 50 mM sodium acetate buffer, pH 6.0, to obtain a crude enzyme preparation which contained 179 mg protein. This crude enzyme preparation was then applied to a Sepharose 6B column (2.5×80 cm) which equilibrated with 50 mM sodium acetate buffer, pH 6.0. The column was eluted with the same buffer at 40 ml per hour, and 5-ml fractions were collected. FIG. 4 shows the elution profile monitored for the absorbance at 280 nm (protein), and for the activities of ceramide-glycanase, α-N-acetylgalactosaminidase and β-hexosaminidase. The effluent from the column was divided into five fractions as shown in FIG. 4. Proteins in these five fractions were separately precipitated by the addition of solid ammonium sulfate to 80% saturation, dissolved in a minimal amount of 50 mM sodium phosphate buffer, pH 6.0, and dialyzed against the same buffer to remove ammonium sulfate. Table I summarizes the amount of protein and ceramide-glycanase in these fractions.

TABLE I

Earthworm Ceramide-Glycanase Activity in the Five Fractions Obtained From Sepharose 6B Chromatography as Shown in FIG. 4

| Fraction No. | Volume (ml) | Protein (mg) | Cer-glycanase (Units[a]) | Specific Activity (Units/mg Protein) |
|---|---|---|---|---|
| I | 3.7 | 9.4 | 7.5 | 0.80 |
| II | 5.6 | 24.4 | 36.8 | 1.51 |
| III | 5.6 | 17.0 | 72.8 | 4.28 |
| IV | 7.0 | 63.0 | 91.3 | 1.45 |
| V | 6.5 | 25.4 | 2.9 | 0.11 |

[a]1 unit = The amount of enzyme that hydrolyzes 1 nmol of GM2 per h.

As shown in this table, among the five fractions, the specific activity of ceramide-glycanase was found to be highest in Fraction III. However, this fraction also ontained a considerable amount of α-N-acetylgalactosaminidase, β-galactosidase and β-hexosaminidase activities. In order to remove exo-glycosidases, Fraction III was passed through an Octyl-Sepharose column (0.7×7 cm) previously equilibrated with 50 mM sodium phosphate buffer, pH 6.0. The column was then washed with the same buffer. Under this condition, exo-glycosidases were not retained by the column. The ceramide-glycanase retained by the column was eluted with 10 ml of 50 mM sodium phosphate buffer, pH 6.0 containing 0.1% Triton X-100 and 40% ethylene glycol. The eluate was subsequently concentrated by ultrafiltration using an Amicon PM-10 membrane and dialyzed exhaustively against 50 mM sodium phosphate buffer, pH 6.0 to yield 2.2 ml, which contained 52.3 units of ceramide-glycanase and 2.1 mg of protein.

Example 5

Hydrolysis of GlYoolipids with Earthworm Enzyme

The assay for ceramide-glycanase was carried out essentially according to the method described above in Example 3. The incubation mixture contained the following components in 0.2 ml: glycolipid substrate, 20 nmol; sodium acetate buffer (50 mM), pH 4.5; sodium taurodeoxycholate, 400 μg; and 20 μl of the enzyme solution of Example 4 containing 56 μg protein. Glycolipid substrates included LacCer, GbOse₃Cer, GT1, diGalCer, GalCers and GlcCer. After incubating at 37° C. for 16 hours, 5 volumes of chloroform:methanol (2:1) were added to the reaction mixture to terminate the reaction. The mixture was vortexed and centrifuged to separate the organic phase (lower) from the aqueous phase (upper). These two phases were separately evaporated to dryness. For the detection of the released oligosaccharide, the aqueous phase was analyzed by TLC using n-butanol:acetic acid:$H_2O$ (2:1:1) as the developing solvent. Sialic acid-containing glycoconjugates were revealed by resorcinol spray, while the glycoconjugates which contained neutral sugars were visualized by diphenylamine spray. For the detection of the ceramides released by ceramide-glycanase, the organic phase was analyzed by TLC using chloroform:methanol (9:1) as the developing solvent. The ceramides were revealed by staining the plate with Coomassie brilliant blue. The chromatograms are seen in FIGS. 5 and 6.

For quantitative analysis of the oligosaccharide released, the reaction mixture was similar to that described above, except 30 nmol of $^3$[H]-labeled GM1 (1.5x10$^4$ cpm) was used as the substrate. After incubation, the reaction was terminated by heating the tube in a bath of boiling water for 3 minutes. The liberated radioactive oligosaccharide was determined by dialysis. Briefly, the reaction mixture was dialyzed against 2 ml of distilled water overnight at room temperature in a shaker. Then, an aliquot of the dialysate containing the liberated radioactive oligosaccharide was mixed with scintillation fluid, and the radioactivity was measured by liquid scintillation counting. One unit of ceramide-glycanase is defined as the amount which hydrolyzes 1 nmol of GM2 per hour under the above assay conditions. Exo-glycosidass were assayed by using p-nitrophenyl-glycosides as substrates. Protein was determined by the method of Lowry et al as described above in Example 3 using bovine serum albumin as standard.

The earthworm ceramide-glycanase of Example 4 was found to be completely free from exo-glycosidases. By using tritium-labeled GM2 as the substrate, the optimal pH of earthworm ceramide-glycanase was found to be around 4.5. As in the case of the eech ceramide-glycanase, the earthworm ceramide-glycanase was also retained by Octyl-Sepharose and the enzyme required the presence of sodium taurodeoxycholate to carry out the hydrolysis. LacCer was the shortest glycosphingolipid hydrolyzed by the enzyme. DiGalCer (Galα1→4GalCer), however, was not hydrolyzed. The two most common monohexosylceramides, GalCer and GlcCer, were also found to be refractory to the earthworm ceramide-glycanase.

Figure 5A:
FIG. 5 is photographs of thin-layer chromatograms showing th release of the ceramides (A) and the oligosaccharides (B) from various neutral glycosphingolipids in which one unit of earthworm ceramide-glycanase containing 40 μg protein was separately incubated with variuos neutral glycosphingolipids at 37° C. for 17 h under the conditions described in Example 5, and in which in chromatogram A, lane E is enzyme; lane S-1 is standard ceramide containing nonhydroxy fatty acids; lane S-2 is standard ceramide containing α-hydroxy fatty acids; lane Lc is LacCer; lane $Gb_3$ is $GbOse_3Cer$; lane $Gb_4$ is $GbOse_4Cer$; lane $Gb_5$ is $GbOse_5Cer$; and in chromatogram B the lanes are identical to those in chromatogram A except that S-1 is standard containing GalNAc, lactose, trisaccharide from $GbOse_3Cer$ (top to bottom) and S-2 is oligosaccharides from $GbOse_4Cer$ (top) and $GbOse_5Cer$.
Figure 5B:
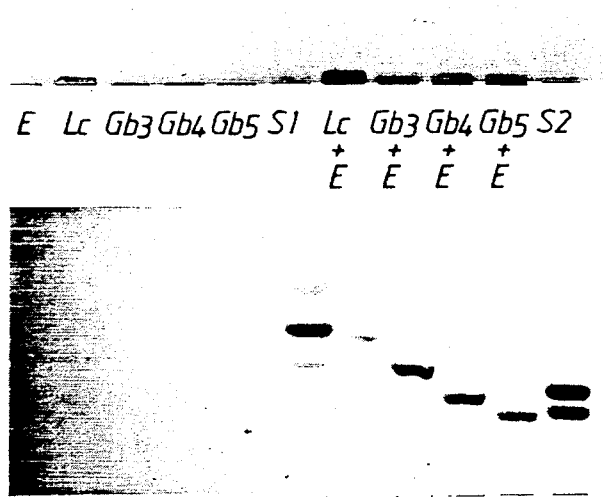

As shown in FIG. 5A, the earthworm ceramide-glycanase was able to release ceramides from GbOse$_5$Cer, GbOse$_4$Cer, GbOse$_3$Cer and LacCer. FIG. 5B shows the release of the intaot oligosaccharide from these glycolipids. The enzyme liberated a pentasaccharide, a tetrasaccharide, a trisaccharide and a disaccharide, respectively, from GbOse$_5$Cer, GbOse$_4$Cer and LacCer. The 30 GbOsesCer, TLC-mobility of these oligosaccharides were found to be identical to that derived from these glycolipids by the leech ceramide-glycanase. In all cases no release of monosaccharide was detected in the reaction mixture.

Figure 6A:
Figure 6B:
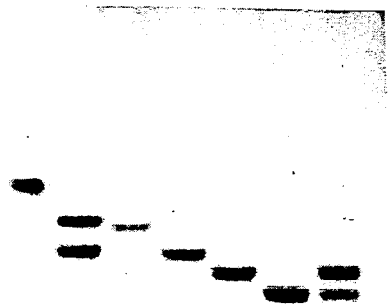

Earthworm ceramide-glycanase was also able to release ceramides from GM3, GM2, GM1 and GD1a as shown in FIG. 6A. FIG. 6B shows the liberation of the intact sialic acid-containing oligosaccharide from each of the above mentioned gangliosides by the earthworm ceramide-glycanase. From GM2, GM1 and GD1a, the enzyme released an intact sialic acid-containing oligosaccharide with TLC-mobility identical to the standard oligosaccharide prepared from the respective ganglioside by ozonolysis. These results clearly show that the earthworm, *Lumbricus terrestris*, and the leeches, *Hirudo medicinalis* and *Macrobdella decora* contain ceramide-glycanase. The earthworms collected in the vicinity of New Orleans, La. were also found to contain this enzyme.

The possible presence of ceramide-glycanase in other organisms was also considered. Since leeches are blood sucking, it was expected that ceramide-glycanase might occur in other blood sucking organisms. However, this enzyme was not found in such blood sucking organisms as mosquitoes (*Aedes aegypti* (Linnaeus) and *Culex quinquefasciatus* Say, either male or female), ticks (*Ornithodoros tartakovskyi*) or triatomine bug (*Rhodnius prolixus*). On the other hand, while both leeches and earthworms are annelids and are phylogenetically closely related, it is interesting to note that the digestive tract of the earthworm contains very little ceramide-glycanase activity. In addition, the anterior portion of leeches which contained no digestive organs was also found to contain ceramide-glycanase. As earthworms are neither blood suoking nor carnivorous, the presence of ceramide-glycanase in the tissues of earthworm must have other biological functions which are presently not fully understood.

Since ceramide-glycanase can release the intact oligosaccharide and ceramide from glycosphingolipids, it is a very useful tool for the structural analysis of glycosphingolipids. Because of their wide availability, earthworms are a convenient source for the preparation of ceramide-glycanase.

Having described the invention hereinabove, many variations in the materials, steps and equipment will occur to those skilled in the art. The claims which follow are intended to embrace all such variations with the scope and spirit thereof.

We claim:

1. A protein composition comprising ceramide-glycanase which functions to hydrolyze the glycosidic linkage of a glycolipid to yield an intact oligosaccharide and a lipid.

2. The protein composition of claim 1, wherein the ceramide-glycanase activity is at least about 1 unit per milligram of protein.

3. The protein composition of claim 1, wherein the ceramide-glycanase activity is at least about 50 units per milligram of protein.

4. The protein composition of claim 1, wherein the ceramide-glycanase activity is at least about 2000 units per milligram protein.

5. The protein composition of claim 1, wherein the ceramide-glycanase activity is about 200014 6000 units per milligram of protein.

6. The protein of claim 1, wherein said protein comprises annelid ceramide-glycanase.

7. A ceramide-glycanase enzyme which functions to hydrolyze the glycosidic linkage of a glycolipid to yield an intact oligosaccharide and a lipid, and which is essentially free of exoglycosidase.

8. The enzyme of claim 7, wherein enzyme is annelid ceramide-glycanase.

9. The enzyme of claim 7, wherein said ceramide-glycanase hydrolyzes glycosphingolipid at the glycosidic bond between the ceramide and the glycan thereof wherein the glycan is an oligosaccharide or higher polysaccharide.

10. The enzyme of claim 9, wherein the glycan and the ceramide ar essentially released intact.

11. The enzyme of claim 10, wherein the ceramide-glycanase has an optimum pH between about 4.5 and about 6.5.

12. The enzyme of claim 7, wherein said ceramide-glycanase is obtained by a method comprising:
preparing extract of annelid muscle; fractionating protein from said extract; and purifying said protein by gel permeation chromatography to substantially remove exo-glycosidases therefrom.

13. The enzyme of claim 11, wherein said enzyme is derived from an annelid source.

14. The enzyme of claim 13, wherein said annelid is a species of Lumbricidae.

15. The enzyme of claim 13 wherein said annelid is a species of Hirudinea or Macrobdellae.

16. The enzyme of claim 13, wherein said annelid is a species of Nereis.

17. A method for hydrolyzing glycolipids comprising:
contacting a substrate with ceramide-glycanase essentially free of other glycosidases for a time and under conditions effective to substantially hydrolyze said substrate into products including substantially intact oligosaccharide, said substrate selected from the group consisting essentially of glycoconjugates in which the glycan has at least two saccharides in a chain, the aglycon is hydrophobic and the glycan is glycosidically bonded to the aglycon.

18. The method of claim 17, wherein said contact is in the presence of a detergent.

19. The method of claim 18, wherein said detergent comprises bile salts.

20. The method of claim 17, wherein said substrate includes glycosphingolipids.

21. The method of claim 17, wherein said substrate includes gangliosides.

22. The method of claim 16, wherein said substrate includes alkylglycolipids or α-hydroxyalkylglycolipids in which the aglycon has at least 8 carbon atoms.

23. The method of claim 17, further comprising separating the products of the hydrolyzed substrate.

24. The method of claim 23, wherein said separation comprises solvent extraction.

25. The method of claim 23, wherein said separation comprises thin-layer chromatography.

26. The method of claim 23, further comprising recovering said oligosaccharide.

27. A method for recovering purified ceramide-glycanase from annelids comprising:
preparing annelid extract in an extraction solvent;
fractionating proteins in the annelid extract;
recovering the protein fraction containing ceramide-glycanase; and
purifying said ceramide-glycanase protein by chromatography.

28. The method of claim 27, wherein said extract preparation comprises homogenizing annelid in water.

29. The method of claim 28, wherein said annelid includes muscle tissue.

30. The method of claim 29, further comprising removing digestive organs from said muscle prior to said homogenization.

31. The method of claim 28, wherein said fractionation includes precipitation of said protein with ammonium sulfate at up to 80% saturation of said extract.

32. The method of claim 27, wherein said chromatography includes elution of said protein on a molecular sieve column and recovery of an eluate having a ceramide-glycanase activity of at least 1 unit per milligram of protein in said eluate.

33. The method of claim 32, wherein said molecular sieve is permeation gel.

34. The method of claim 32, wherein said column is an agarose column.

35. The method of claim 33, wherein said chromatography further includes elution of said molecular sieve eluate on a hydrophobic interaction column and recovery of an eluate therefrom having a ceramide-glycanase activity of at least about 50 units per milligram of protein therein.

36. The method of claim 35, wherein said hydrophobic interaction column is an octyl-agarose or Phenyl-agarose column which substantially adsorbs said ceramide-glycanase and said elution thereon includes a first wash to remove unadsorbed exo-glycosidases from said column and a second wash with a solvent containing detergent to elute said ceramide-glycanase.

37. The method of claim 36, wherein said hydrophobic-interaction column eluate has a ceramide-glycanase activity of at least about 2000 units per milligram of protein therein.

38. The method of claim 27, wherein said annelid is leech, earthworm or nereis.

* * * * *